(12) United States Patent
Wu et al.

(10) Patent No.: US 9,427,592 B2
(45) Date of Patent: Aug. 30, 2016

(54) SYSTEMS AND METHODS FOR LOW ENERGY WAKE-UP AND PAIRING FOR USE WITH IMPLANTABLE MEDICAL DEVICES

(71) Applicant: Pacesetter, Inc., Los Gatos, CA (US)

(72) Inventors: Yongjian Wu, Saratoga, CA (US); Chao-Wen Young, Cupertino, CA (US); Jun Yang, Valencia, CA (US); Reza Shahandeh, Thousand Oaks, CA (US); Thanh Tieu, Simi Valley, CA (US); Min Yang, Los Altos, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 157 days.

(21) Appl. No.: 14/012,634

(22) Filed: Aug. 28, 2013

(65) Prior Publication Data

US 2015/0065047 A1 Mar. 5, 2015

(51) Int. Cl.
*A61N 1/372* (2006.01)
*H04W 4/00* (2009.01)
*A61N 1/36* (2006.01)

(52) U.S. Cl.
CPC .......... *A61N 1/37252* (2013.01); *H04W 4/008* (2013.01); *A61N 1/36071* (2013.01); *A61N 1/37235* (2013.01); *A61N 1/37276* (2013.01)

(58) Field of Classification Search
CPC ............ H04W 52/0229; Y02B 60/50; A61N 1/37276; A61N 1/3605; A61N 1/08; A61N 1/37252; A61B 5/0006; A61B 5/145; A61B 5/0428; A61B 2560/0209; G06F 9/485
See application file for complete search history.

(56) References Cited

U.S. PATENT DOCUMENTS

| | | | |
|---|---|---|---|
| 7,416,530 B2 | 8/2008 | Turner et al. | 600/485 |
| 8,285,328 B2 | 10/2012 | Caffey et al. | 455/557 |
| 8,315,708 B2 | 11/2012 | Berthelsdorf et al. | 607/60 |
| 2007/0049991 A1* | 3/2007 | Klostermann et al. | 607/60 |
| 2008/0058900 A1 | 3/2008 | Berthelsdorf et al. | 607/59 |
| 2009/0083455 A1* | 3/2009 | Sun et al. | 710/46 |
| 2009/0157127 A1* | 6/2009 | Sowder et al. | 607/4 |
| 2009/0248115 A1* | 10/2009 | Corndorf et al. | 607/60 |
| 2010/0312188 A1* | 12/2010 | Robertson et al. | 604/156 |

(Continued)

FOREIGN PATENT DOCUMENTS

| | | | |
|---|---|---|---|
| EP | 1 895 438 | 7/2007 | G06F 19/00 |
| EP | 1 583 585 | 6/2008 | A61N 1/372 |

(Continued)

*Primary Examiner* — Ping Hsieh
*Assistant Examiner* — James Yang
(74) *Attorney, Agent, or Firm* — Theresa A. Raymer

(57) ABSTRACT

Techniques are provided for use with implantable medical devices or trial medical devices for wirelessly connecting the devices to external instruments such as tablet computers or smartphones. In an example where the medical device is an implantable neurostimulator, the neurostimulator passively detects wireless wake-up signals generated by the external instrument, i.e. the neurostimulator "sniffs" for advertisement signals generated by the external instrument. In response to passive detection of a wake-up signal, the implantable neurostimulator determines if a response is warranted and, if so, the neurostimulator activates its wireless transmission components to transmit an acknowledgement signal to the external instrument so as to complete a wake-up and handshake protocol. In this manner, power consumption within the implantable device (or within a similarly equipped trial medical device) can be reduced compared to devices that would otherwise periodically transmit advertisement signals even when no external mobile instrument is present.

23 Claims, 6 Drawing Sheets

(56) References Cited

U.S. PATENT DOCUMENTS

| | | | |
|---|---|---|---|
| 2011/0202113 A1* | 8/2011 | Persson et al. | 607/60 |
| 2012/0093245 A1* | 4/2012 | Makdissi | A61B 5/0028 375/259 |
| 2012/0215286 A1* | 8/2012 | Rahman | 607/60 |
| 2012/0220351 A1* | 8/2012 | Kerai et al. | 455/574 |
| 2013/0004925 A1 | 1/2013 | Labbe et al. | 434/262 |
| 2013/0030255 A1 | 1/2013 | Embry, II | 600/399 |
| 2013/0102251 A1 | 4/2013 | Linde et al. | 455/41.2 |
| 2013/0165819 A1 | 6/2013 | Tieu | 600/595 |
| 2013/0238056 A1* | 9/2013 | Poore et al. | 607/60 |

FOREIGN PATENT DOCUMENTS

| | | | |
|---|---|---|---|
| EP | 2 426 865 | 3/2012 | H04L 12/28 |
| EP | 2 540 343 | 6/2012 | A61N 1/372 |

\* cited by examiner

POWER INEFFICIENT WAKEUP/HAND SHAKE PROTOCOL

POWER EFFICIENT WAKEUP/HAND SHAKE PROTOCOL

SYSTEMS AND METHODS FOR LOW ENERGY WAKE-UP AND PAIRING FOR USE WITH IMPLANTABLE MEDICAL DEVICES

FIELD OF THE INVENTION

The invention generally relates to implantable medical devices such as full or trial neurostimulation devices and, in particular, to techniques for controlling communication between such devices and external mobile computing instruments such as smartphones and tablet computers.

BACKGROUND OF THE INVENTION

Implantable neurostimulation devices can be employed to manage pain arising from a variety of conditions such as failed back surgery syndrome, post-laminectomy syndrome or other neuropathies. To this end, a spinal cord stimulation (SCS) device or other neurostimulator may be implanted within the body to deliver electrical pulses to nerves or other tissues. The neurostimulator typically includes a small pulse generator device similar to a pacemaker but equipped to send electrical pulses to leads mounted along the nerves near the spinal cord or elsewhere. For SCS, the generator is often implanted in the abdomen or buttock area. The stimulation leads may include thin wires or paddles for delivering electrical pulses to patient nerve tissues. An external controller, similar to a remote control device, may be provided to allow the patient to control or adjust the neurostimulation. Currently, prior to permanent (i.e. chronic) implant of a neurostimulator, the patient undergoes a trial period during which he or she is implanted with a lead that is externalized and connected to a trial neurostimulation control device, which the patient carries with him or her. Herein, the external neurostimulation control device used during the trial period is referred to as a trial neurostimulator or trial neurostimulation device.

State-of-the-art implantable neurostimulators and trial neurostimulators are being designed to communicate with tablet computers, smartphones and other mobile instruments to allow the patient or clinician to control the operation of the device, retrieve diagnostic data, etc. For example, dedicated application software (i.e. an "app") running on a tablet computer could be used to adjust the frequency or amplitude of neurostimulation applied to the spine by an SCS device to allow the patient to improve pain reduction. In particular, Bluetooth Low Energy (BLE) telemetry protocols can be used to control communication between a mobile instrument and an implantable neurostimulator or trial neurostimulator. Issues, however, arise in implementing such a communication scheme. App designers typically have minimal control over the behavior of the mobile device platform, which may comprise a commercially off-the-shelf mobile instrument employing build-in drivers and operating systems. The designers of apps for communicating with neurostimulation devices may have only a limited level of configuration control on the BLE protocol stack. Furthermore, conservation of the power supply of an implantable medical device is a key design issue. It is important to avoid undue depletion of battery resources. This is particularly true insofar as "wake-up and pairing" is concerned wherein the implantable neurostimulator and the mobile instrument detect one another's presence and establish secure communications. Similar concerns apply to external trial neurostimulators, which may be provided with only minimal power resources since the trial period is typically a month or less. Accordingly, there is the need to implement a wake-up and pairing scheme that provides a robust link with minimal impact on the longevity of neurostimulator devices or other implantable or trial medical devices.

However, the standard wake-up and pairing scheme for connecting a Bluetooth accessory device (i.e. a slave device) to a mobile instrument (such as a tablet computer) is for the accessory device to periodically "advertise" itself so that a mobile instrument in the vicinity might be alerted to its presence. The mobile instrument then tags to one of the advertising pulses and requests a connection, i.e. an initial "handshake" is performed. Pairing or normal link establishment then follows the initial handshake. However, most of the advertisement signals generated by the accessory device are unheeded because no mobile instrument is nearby to establish a connection. For implantable neurostimulators, the standard wake-up and pairing scheme could significantly deplete the battery resources of the implanted device. Similar battery depletion problems can arise during a trial neurostimulation period when wirelessly connecting an external trial neurostimulator to a mobile instrument. Still further, problems can arise involving malicious "spoofing" or "hacking" if the neurostimulator is programmed to transmit frequent advertisement signals that a rogue external instrument might intercept. Indeed, even if the neurostimulator properly rejects communication requests with a rogue device, considerable battery energy could be wasted while the neurostimulator filters out the invalid requests. Similar problems could also occur with other implantable medical devices such as pacemakers if equipped to communicate with external instruments using Bluetooth or other wireless communication protocols.

Accordingly, it would be highly desirable to provide improved techniques for performing wake-up and pairing (or similar protocols) between implantable/external medical devices and mobile instruments such as tablet computers. It is to these ends that aspects of the invention are generally directed.

SUMMARY OF THE INVENTION

In an exemplary embodiment, a method is provided for use with an implantable medical device or trial medical device to wirelessly connect the device to an external instrument such as a tablet computer or smartphone. In one example, where the medical device is an implantable device such as an SCS device, the implantable device passively detects wireless wake-up signals generated by the external instrument, e.g. the implantable device "sniffs" for advertisement signals generated by the external instrument. In response to passive detection of a wake-up signal from the external instrument, the implantable device determines if a response is warranted (i.e. the detected signal is a valid wake-up signal) and, if so, the implantable device activates its wireless transmission components to transmit an acknowledgement signal to the external instrument so as to complete a wake-up and handshake protocol. Hence, rather than have the implantable device generate and transmit advertisement signals for the external instrument to detect, the external instrument is instead programmed to generate advertisement signals that the implantable device passively detects and selectively responds to. The implantable device does not proceed to link establishment unless a valid wake-up signal is received from an authorized external instrument. In this manner, power consumption within the implantable medical device (or within a similarly equipped trial medical device) can be reduced compared to devices that would otherwise periodically generate and transmit advertisement signals even when no authorized external instrument is present. Still further, the risk that the medical device might be "spoofed" or "hacked" by a rogue device is reduced since the medical device only responds to valid advertisement signals from a properly authorized external instrument. Moreover, the medical device need not waste energy filtering out frequent communication requests from rogue devices, since the medical device will not be advertising itself to those devices.

In an illustrative embodiment, the implantable device is a neurostimulator and the external instrument is a mobile device (e.g. tablet computer, smartphone, etc.) The neurostimulator and the external mobile instrument are both Bluetooth-enabled devices equipped to implement BLE communication protocols or standards. Telemetry components of the implantable neurostimulator remain in a sleep mode until a passive detection cycle is initiated which may occur, for example, once every five to ten seconds. During the passive detection cycle, the neurostimulator "sniffs" for BLE advertisement signals generated by any mobile instruments that might be in the vicinity. If no such signal is detected, the telemetry components return to the sleep mode pending the next sensing cycle. Assuming, however, that a BLE advertisement signal is detected, the neurostimulator examines the advertisement signal to determine if it represents a valid wake-up signal that warrants a response, e.g. the signal includes appropriate identification codes indicating it was sent by a device authorized to communicate with the particular neurostimulator. If the advertisement signal is deemed to be a valid wake-up signal, the neurostimulator activates its signal transmission components to transmit a suitable responsive handshake signal to the mobile instrument. Thereafter, the mobile instrument can transmit appropriate signals to the neurostimulator to, for example, retrieve diagnostic data from device memory for display on the mobile instrument or to adjust the programming of the neurostimulator. In examples where the neurostimulator is an SCS device, the mobile instrument might be used to change the frequency, duration or amplitude of SCS. Further improvement on the discovery latency can be achieve by making the external instrument perform active advertising upon app activation by the user.

Still further, in the illustrative embodiment, the advertisement signals generated by the mobile instrument are generated only in response to user input provided via an application specific program ("app") whereupon the mobile instrument transmits a burst of "advert" signals with one signal every 20 milliseconds (ms) or so. Such bursts of advert signals can be repeated during an interval of five to ten seconds to allow the neurostimulator to detect the signals during one of its sensing cycles to permit wake-up and handshake. (By setting the sensing cycle of the neurostimulator to five to ten seconds, the latency between a communication request from the mobile instrument and its acknowledgement is generally acceptable, i.e. it is not too long.) Thereafter, further wireless communications proceed under the control of the user via the software app until the user terminates the communication session or either the neurostimulator or the mobile instrument otherwise terminates the session. By having the mobile instrument only generate advert signals in response to user input, the procedure also helps avoid undue depletion of power resources of the mobile instrument.

Although described herein primarily with respect to communications between an implantable medical device and an external mobile computing device such as a tablet computer, aspects of the invention are also applicable to communications between external instruments and trial medical devices that are external to the patient but include one or more leads for implant within the patient, or to trial medical devices for removable implant within the patient.

System and method examples are described in detail below.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Neurostimulation System and External Mobile instrument

Figure 1:
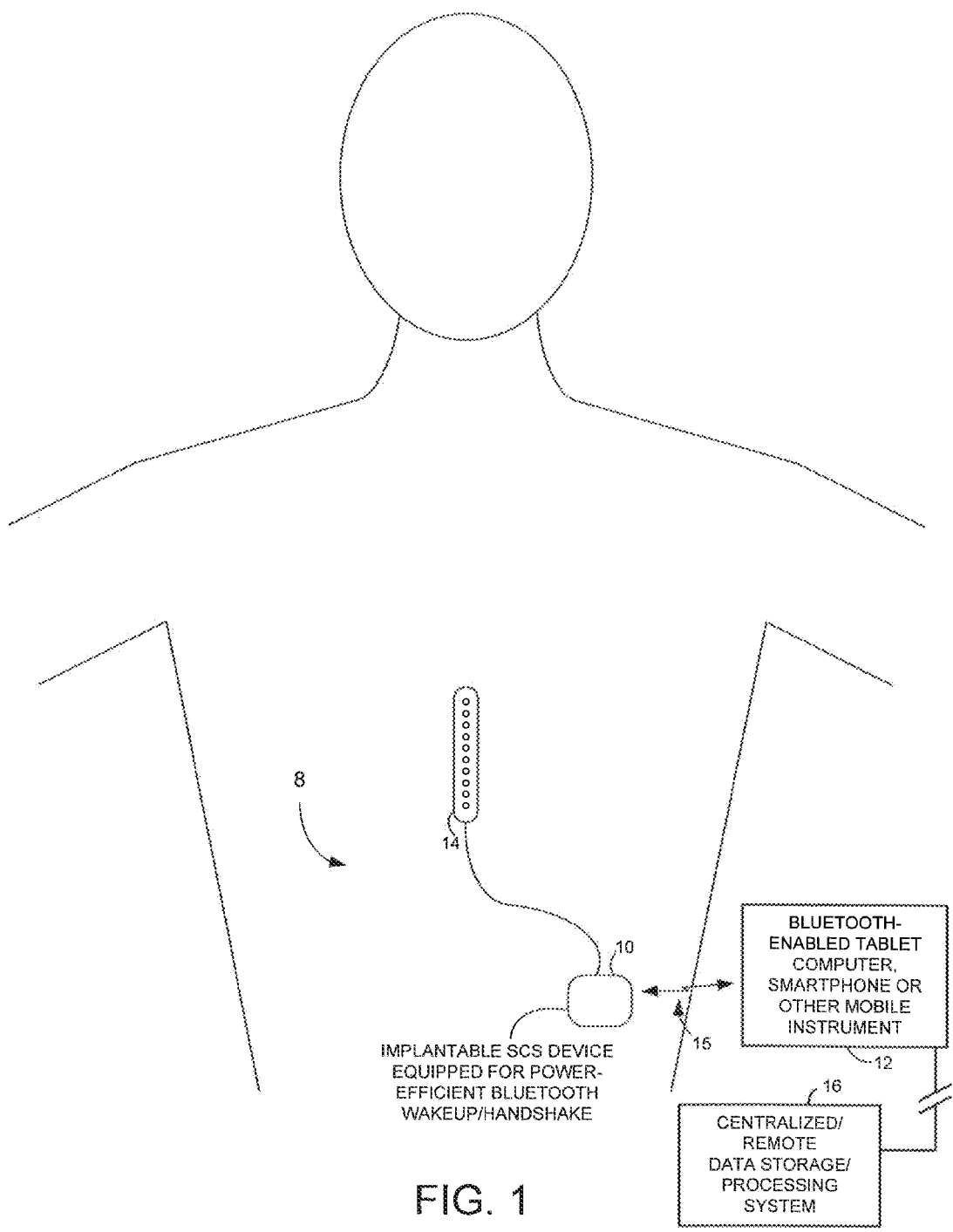
FIG. 1 illustrates an exemplary neurostimulation system having an implantable SCS device equipped for power-efficient wake-up/handshake with a mobile instrument such as a tablet computer.

FIG. 1 illustrates an exemplary implantable medical system 8 having an implantable SCS device 10 (or "pulse generator") equipped for power-efficient wake-up/handshake with an external mobile instrument 12 such as a tablet computer or smartphone, which may be referred to as a "Neuro External" device. SCS device 10 includes one or more paddles or electrodes 14 implanted along the spine for delivering neurostimulation using one or more stimulation sets (Stim Sets) initially specified by a clinician. The Stim Sets specify SCS parameters for controlling delivery of SCS to nerve tissues of the patient to address the needs of the patient, such as to reduce pain or to achieve desired cardio-protective effects. The clinician or the patient can then change the Stim Sets using the mobile instrument (via a Bluetooth wireless radio communication link 15) to activate, deactivate or adjust the neurostimulation, such as by changing the amplitude, frequency or duration of stimulation pulses generated by the SCS device. The mobile instrument can also be used to retrieve diagnostic data from the SCS device including data pertaining to remaining battery power (i.e. battery life) or other operational parameters of the device. As will be explained in more detail below, communication between the SOS device and the mobile instrument preferably exploits a power-efficient wake-up/handshake protocol that reduces overall power consumption by the SCS device while also reducing the risk of "spoofing" or "hacking" by rogue external instruments.

Mobile instrument 12 may also communicate with a remote or centralized data processing/data storage system 16 via the Internet or other suitable communication channels/networks to relay information to the primary care physician of the patient or to other appropriate clinicians. The centralized system may include such systems as the House-Call™ remote monitoring system or the Merlin@home/Merlin.Net systems of St. Jude Medical. Note that, although the example of FIG. 1 shows an SCS device 10 for stimulating the spinal cord, additional or alternative stimulation devices might be employed, such as devices for stimulating other tissues or organs within the patient. Some patients might additionally or alternatively have an implantable cardiac rhythm management device (CRMD) such as a pacemaker, implantable cardioverter-defibrillator (ICD) or a cardiac resynchronization device (CRT.) At least some of the techniques described herein are generally applicable to any of a variety of implantable medical devices and to any of a variety of external trial devices (such as the trial SCS device shown in FIG. 6, and discussed below.) Note also that FIG. 1 is a stylized illustration that does not necessarily set forth the precise locations of the implantable components nor their relative sizes or shapes.

Exemplary Power-Efficient Wake-Up/Handshake Systems and Methods

Figure 2:
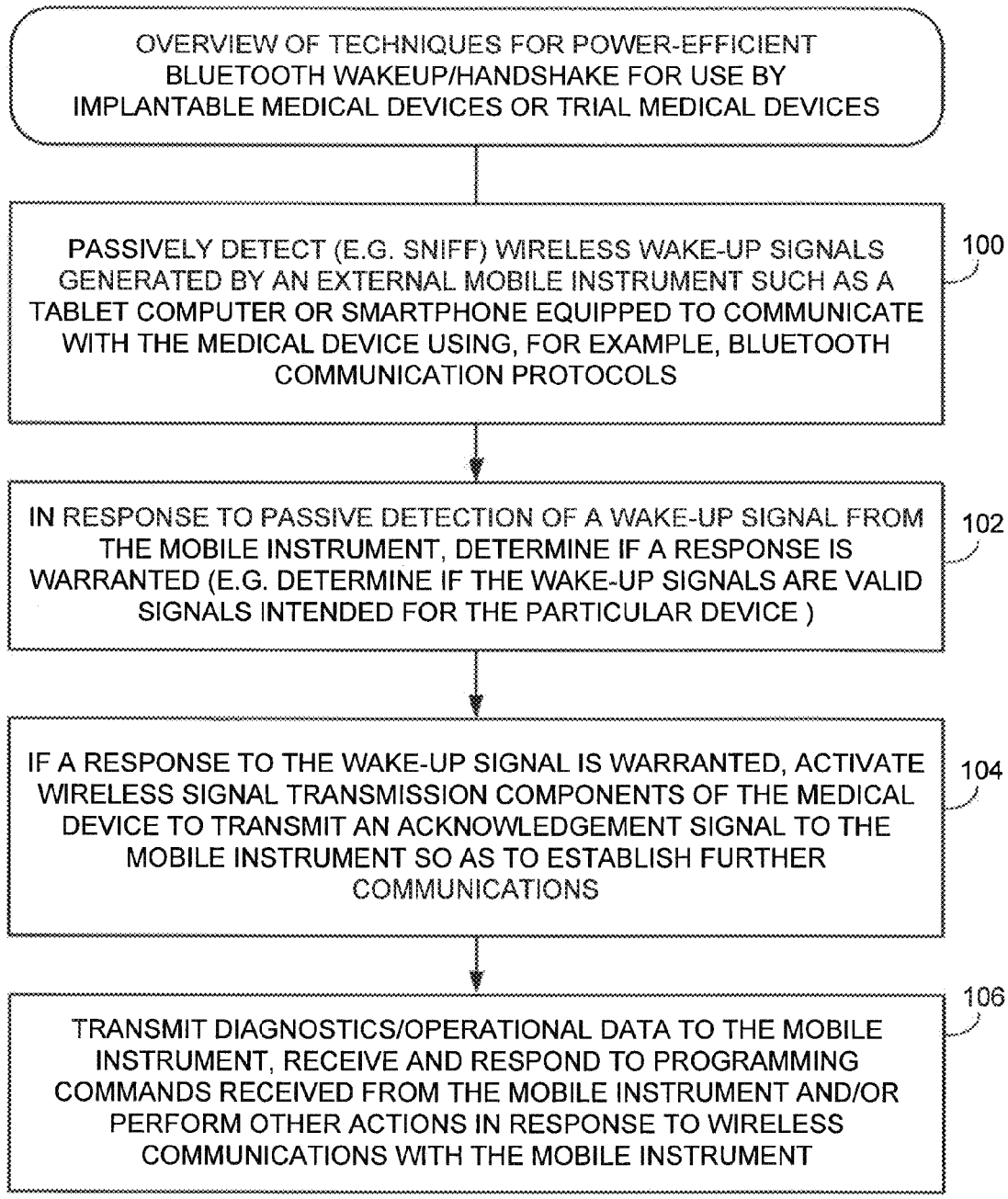
FIG. 2 provides an overview of a power-efficient wake-up/handshake method for use by the implantable medical device of FIG. 1 or similarly-equipped trial medical devices.

FIG. 2 broadly summarizes a power-efficient wake-up/handshake procedure for use by an implantable medical device or external trial medical device. For the purposes of these descriptions, it will be assumed that the device is an implantable medical device such as a chronically-implanted SCS device but it should be understood that corresponding techniques can be used with an external trial medical devices as well. Beginning at step 100, the implantable device passively senses or detects (e.g. sniffs) radio frequency (RF) wireless wake-up signals (e.g. advertisement signals) generated by an external mobile instrument such as a tablet computer or smartphone equipped to communicate with the medical device using Bluetooth communication protocols or other suitable wireless communication protocols. At step 102, in response to passive detection of one or more wake-up signals from the mobile instrument, the implantable device examines the wake-up signals to determine if a response is warranted. In this regard, the implantable device determines if the wake-up signals are valid or legitimate signals sent from an approved mobile instrument running an approved "app" authorized to communicate with the particular implantable device. This may be determined, for example, based on suitable codes within the BLE configuration profile associated with the wake-up signals.

At step 104, if a response to the wake-up signal is warranted, the implantable device activates its wireless signal transmission components to transmit a "handshake" acknowledgement signal to the mobile instrument so as to establish or commence further communications. In this manner, the wireless signal transmission components of the implantable device can remain inactive (e.g. in a sleep mode) until a valid wake-up signal is received. This helps reduce power consumption within the implantable device.

At step 106, once wireless communication is fully established with the mobile instrument, the implantable device: transmits diagnostics/operational data to the mobile instrument; receives and responds to programming commands received from the mobile instrument; and/or performs other suitable actions in response to wireless communications with the mobile instrument.

Hence, with this technique, rather than have the implantable device generate and transmit advertisement signals for the mobile instrument to detect, the mobile instrument is instead required to generate advertisement signals that the implantable device selectively responds to. In this manner, power consumption within the implantable device can be reduced compared to implantable devices that would otherwise periodically generate and transmit advertisement signals even when no mobile instrument is present. Still further, the risk that the implantable device might be "spoofed" or "hacked" by a rogue mobile instrument is reduced. Moreover, the implantable device need not waste energy filtering out frequent communication requests from rogue devices, since the implantable device will not be advertising itself to those devices.

Figure 3:
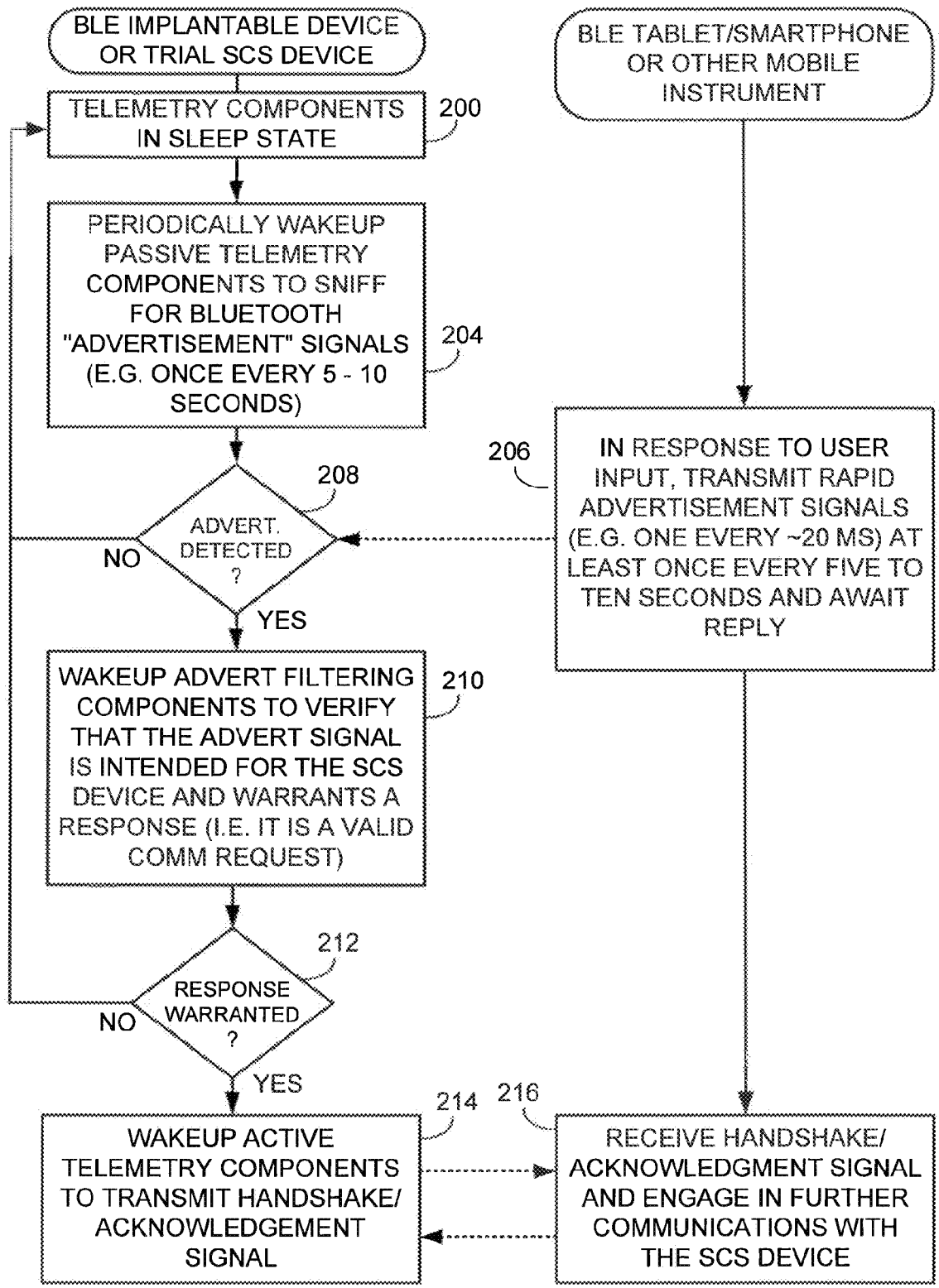
FIG. 3 provides an exemplary power-efficient wake-up/handshake procedure in accordance with the general method of FIG. 2 for an example where an implantable SCS device (or external trial SCS device) communicates with a mobile instrument by exploiting BLE protocols.

FIG. 3 provides further details of an illustrative implementation wherein the implantable medical device (or external trial medical device) as well as the mobile instrument are BLE-enabled devices. In this particular example, the implantable device is an SCS device. At step 200, the telemetry components of the SCS device are in a sleep state to conserve energy. At step 202, the SCS device periodically wakes up its passive telemetry components to "sniff for" or "listen for" Bluetooth advertisement signals, which may be performed, e.g., once every 5-10 seconds (or at other suitable times to meet any latency requirements.) The "passive" telemetry components of the device are those components of the SCS device needed to sense or receive wireless signals. These components may differ from any "active" telemetry components needed to actually transmit wireless signals. Active telemetry components consume considerably more energy within the SCS device than passive components and hence are only activated if needed.

Meanwhile, at step 206, in response to user input (i.e. input from the patient or clinician), the external mobile instrument transmits rapid or dense advertisement signals (e.g. one every ~20 ms, which is within the BLE specified range of ~7.5 ms to 10 seconds) during a period of five to ten seconds and awaits a reply from the SCS device. For example, the patient may be provided with an app for running on a tablet computer (e.g. an iPad™, iPod Touch™, iPad Mini™ or Android™ based tablet), a smartphone (e.g., an iPhone™ or Android™-based cell phone) or other suitable external mobile or portable instruments, wherein the app is programmed and authorized to communicate with the particular SCS device implanted within the patient. If the patient wants to adjust the operation of the SCS device, such as to change the Stim Set, the patient activates the app and instructs the app to initiate communications with the SCS device. In response, the app controls the communication chip of the mobile instrument to transmit the appropriate advertisement signals to allow the SCS device to detect the presence of the mobile instrument. By repeating the advertisement signals at a relatively high frequency (e.g. one every ~20 ms) within a period of five to ten seconds, the mobile instrument can be reasonably assured that the SCS device will sense the signals during one of its sensing cycles (which, as noted, occur every five to ten seconds.) Since these signals are only sent following user instructions, the power supply of the mobile instrument is not unduly affected.

Once an advertisement signal is detected, step 208, the SCS device wakes up or activates its internal advertisement filtering components at step 210 to verify that the advert signal is intended for the particular SCS device and warrants a response (i.e. it is a valid communication request.) The advert filtering components of the SCS device may include various software or hardware components for analyzing or examining the advert signals to determine if a response is warranted. This may include program subroutines running on the microcontroller of the SCS device that examine codes within the advert signal to confirm that the particular app of the particular mobile instrument is authorized to communicate with the particular SCS device. In this manner, the SCS device can properly ignore advertisement signals broadcast by other devices or other apps, particularly any such signals that might be generated by rogue devices seeking to spoof or hack the implantable device.

Assuming a response is warranted at step 212, the SCS device wakes up its active telemetry components at step 214 to transmit a handshake/acknowledgement signal back to the mobile instrument to initiate and establish further communications. The handshake/acknowledgement signals is received at step 216 by the mobile instrument, which then engages in further communications with the SCS device to query for stored diagnostic data, selectively change Stim Sets, etc., as already discussed.

Figure 4:
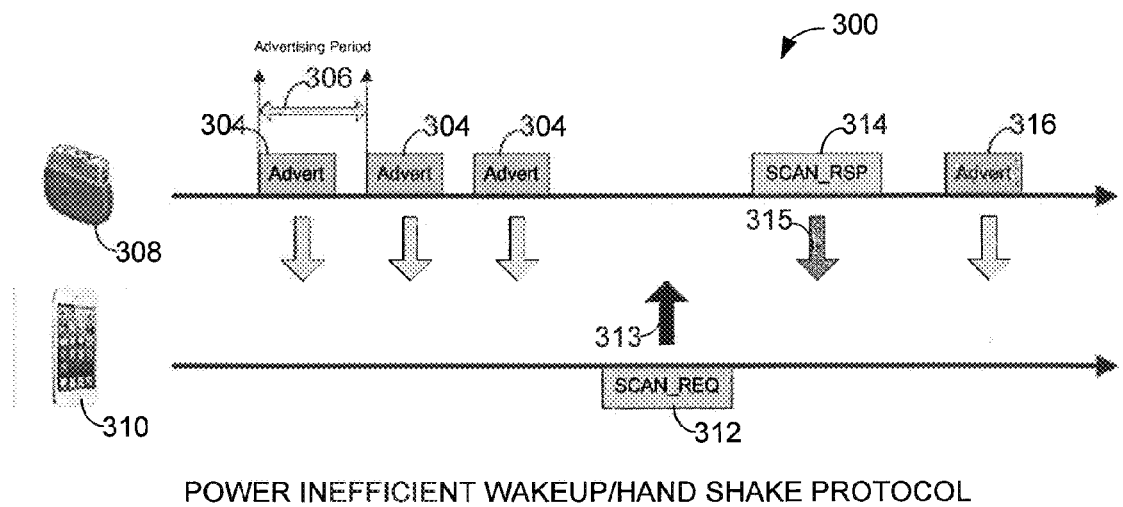
FIG. 4 illustrates exemplary BLE signal sequences for both a power inefficient wake-up/handshake protocol and a preferred power efficient protocol use with the methods of FIGS. 3 and 4.
Figure 4:
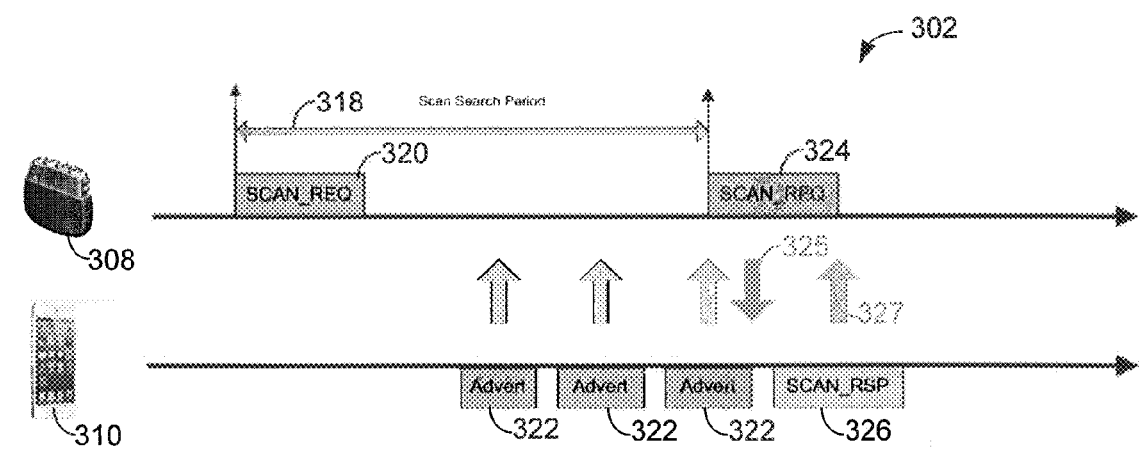

FIG. 4 contrasts a relatively power-inefficient wake-up/handshake protocol 300 with the more power efficient protocol 302 of FIGS. 2 and 3. In the relatively inefficient protocol, advert signals 304 are generated at the beginning of each advertising period 306 by the implantable device 308 (or external trial device), regardless of whether or not there is a nearby mobile instrument 310. If there is no mobile instrument, or if the mobile instrument is not authorized to communicate with the implanted device, then the generation and transmission of the advert signals simply wastes device power. Assuming, though, that an authorized mobile instrument sniffs the advert signals, a SCAN_REQ 312 is generated by the mobile instrument and an acknowledgement signal 313 is sent from the mobile instrument, which in turn triggers a SCAN_RSP 314 within the mobile instrument and a reply signal 315. Eventually, additional advert signals 316 may be generated and transmitted, which again may represent wasted energy if no authorized devices are present. (Note that protocol 300 is not necessarily prior art to the present invention but represents a possible alternative protocol for use with implantable medical devices that would be less power efficient than the improved protocol of the invention.)

In contrast to protocol 300, when using the more power efficient protocol 302 of FIGS. 2 and 3, the implantable device 308 periodically initiates a scan search period 318, which begins with a SCAN_REQ 320. As noted, the scan search period may be five to ten seconds long, depending upon device programming and latency requirements. During at least a portion of this interval, the implantable device sniffs for any advert signals generated by nearby devices. In the example of FIG. 4, a mobile instrument 310 happens to be in the vicinity generating advert signals 322, which are detected by the implantable device. At the completion of the scan search period (at which time another SCAN_REQ 324 occurs), the implantable device issues a responsive acknowledgment signal 325 to the mobile instrument, which responds via a SCAN_RSP 326 and reply signal 327. Hence, in the more efficient wake-up/handshake protocol 302, the mobile instrument does not waste energy generating and transmitting advert signals, but instead responds to those generated by the mobile instrument, thus providing power savings within the implantable device. As already noted, this scheme also reduces the risk of spoofing or hacking since the implantable device is not advertising itself to any and all nearby devices, including any rogue devices. Note also that in these protocols the external instrument can be programmed to carry more information in the adv packets so that the generator can skip scan_xx packets and proceed directly to connect to further save power in the handshaking process.

Figure 5:
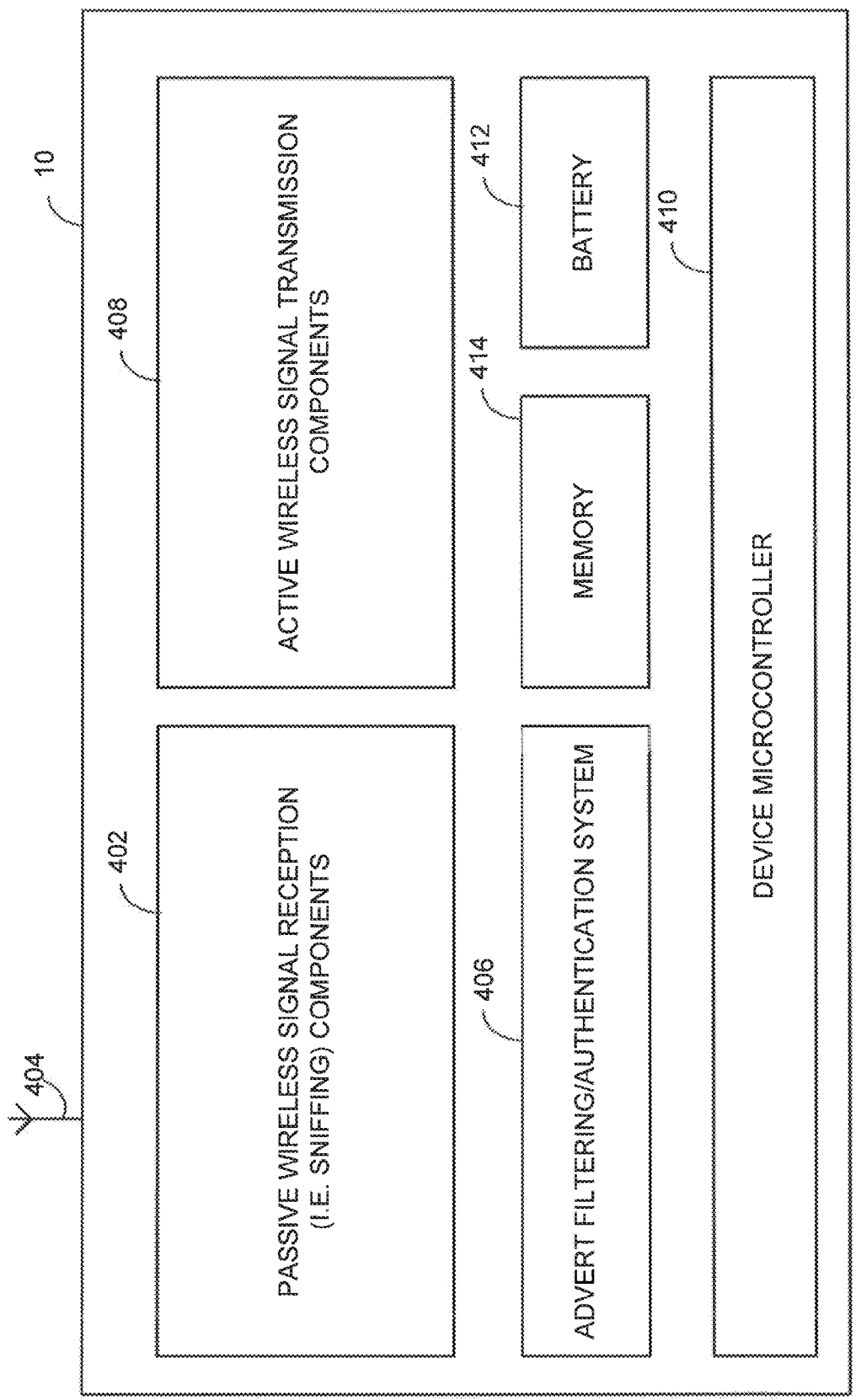
FIG. 5 is a block diagram illustrating pertinent components of the implantable neurostimulator device of FIG. 1.

FIG. 5 provides a block diagram illustrating pertinent components of the implantable device of FIG. 1 for use in implementing the wake-up/handshake protocol of FIGS. 2-4. Briefly, implantable device 10 includes passive wireless signal reception (i.e. sniffing) components 402, which sense or detect RF-based wireless advert signals using an antenna 404 (which may include the case or housing of the device.) If advert signals are detected, an advert filtering/authentication system 406 (or other suitable wake-up signal processing components) determines whether the advert signal warrants a response by, for example, determining whether the advert was issued by an authorized app running on an authorized mobile instrument. Active wireless transmission components 408 of the implantable device generate responsive handshake signals for transmission using the antenna. A controller 410 (such as a microcontroller, application specific integrated circuit (ASIC), etc.) controls the overall operation of the device. Power is supplied by one or more batteries 412. Data is stored within device memory 414. As can be appreciated, numerous other components may be included within the device to allow it to perform its intended functions, such as generating SCS pulses for neurostimulation, sensing nerve signals or electrocardiac signals within the patient, etc.

For further information regarding neurostimulation devices, see, e.g., U.S. patent application Ser. No. 13/442,749 of Xi et al. filed Apr. 9, 2012, entitled "Systems and Methods for Controlling Spinal Cord Stimulation to Improve Stimulation Efficacy for Use By Implantable Medical Devices". As noted, the procedures described herein can also be applied to trial devices. Trial neurostimulation devices are discussed, for example, in U.S. patent application Ser. No. 13/940,727, filed Jul. 12, 2013 of Nabutovsky et al., entitled "Fully Implantable Trial Neurostimulation System Configured for Minimally-Intrusive Implant/Explant", which describes both external trial devices as well as implantable trial devices. RF scanning techniques for use within implantable medical devices are discussed in U.S. Patent Application 2013/0165819 of Tieu, entitled "System and Method for Controlling Radio Frequency Scanning Attributes of an Implantable Medical Device."

Figure 6:
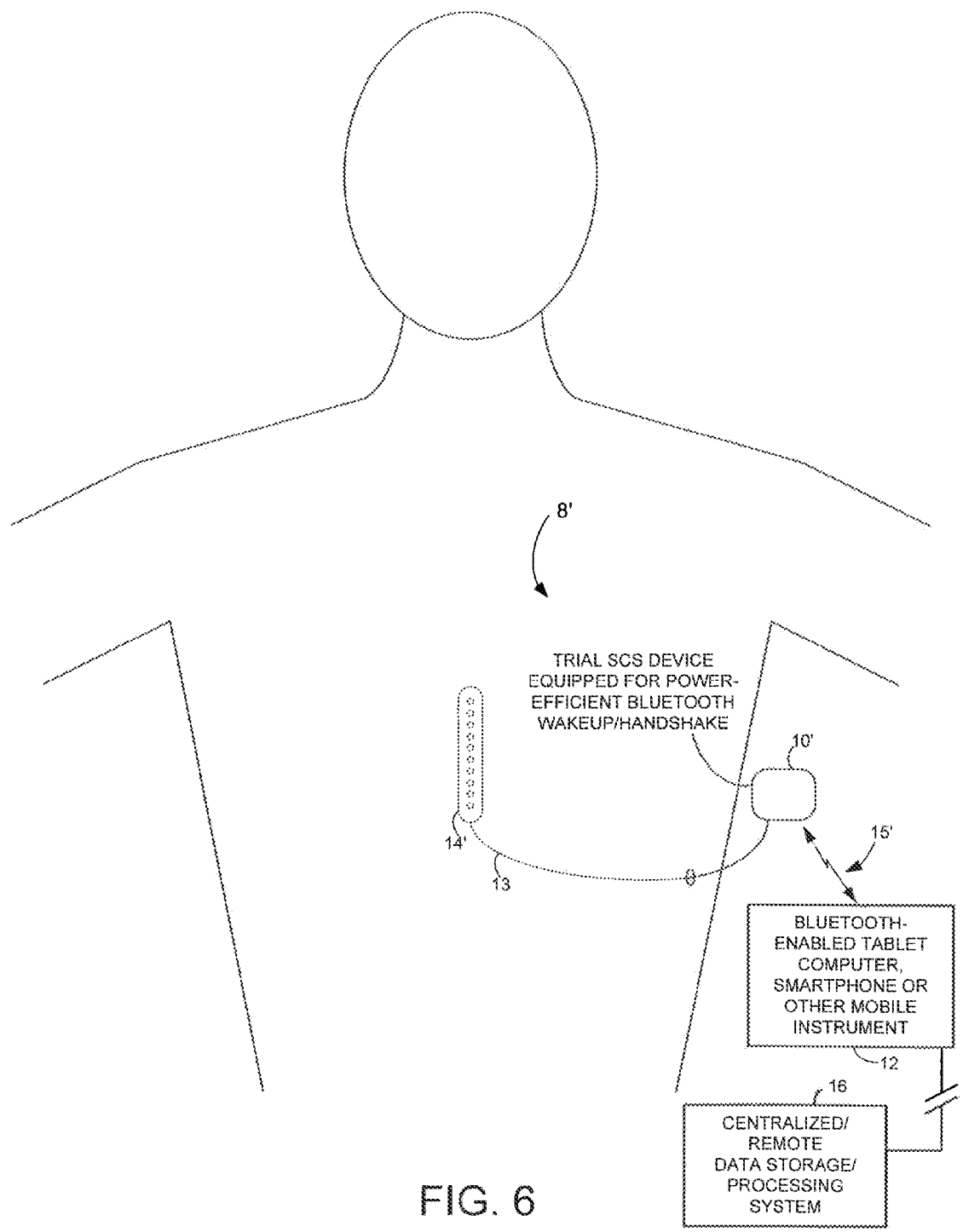
FIG. 6 illustrates an alternative neurostimulation system to that of FIG. 1 wherein the SCS device is an external trial device.

For the sake of completeness, a trial medical device is shown in FIG. 6. Briefly, exemplary trial medical system 8' has an external trial SCS device 10' equipped for power-efficient wake-up/handshake with a mobile instrument 12 such as a tablet computer or smartphone. Trial SCS device 10' includes one or more paddles or electrodes 14' implanted within the patient for delivering trial neurostimulation. In this example, an implantable paddle 14' is connected to the external trial device via a lead 13. In the drawing, phantom lines are used to illustrate the implanted paddle and the portion of lead 13 extending within the body of the patient so as to clearly distinguish between components within the body and those that are external to the patient. The clinician or the patient can use mobile instrument 12 to activate, deactivate or adjust trial neurostimulation via a Bluetooth wireless radio communication link 15'. The mobile instrument can also be used to retrieve diagnostic data from the trial device. Communication between the trial device and the mobile instrument preferably exploits the power-efficient wake-up/handshake protocol described in detail above. The mobile instrument may also communicate with a centralized/remote processing system 16 to relay data to the physician/clinician or for other purposes.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use by an implantable medical device for implant within a patient, the method comprising:
    passively detecting wireless wake-up signals generated by an external instrument equipped to communicate with the implantable medical device, wherein the external instrument is one of a plurality of external instruments capable of communicating with the implantable medical device, and wherein at least some of the plurality of external instruments are not authorized to communicate with the implantable medical device; and
    in response to passive detection of a wake-up signal from the external instrument, determining if a response to the wake-up signal is warranted and, if so, activating wireless signal transmission components of the implantable medical device and transmitting an acknowledgement signal to the external instrument, wherein determining if a response to the wake-up signal is warranted includes determining if the external instrument generating the wake-up signal is authorized to wake up the implantable medical device based on a coded signal received from the external instrument that indicates the external instrument is authorized to wake up the implantable medical device and that differs from coded signals from at least some other external instruments capable of communicating with the implantable medical device but not authorized to wake up the implantable medical device.

2. The method of claim 1 wherein the wake-up signals are short range wireless wake-up signals received by a component of the implantable medical device.

3. The method of claim 2 wherein the short range wireless wake-up signals are advertisement signals generated in accordance with a low energy short range wireless communication standard.

4. The method of claim 2 wherein passively detecting wake-up signals includes short range wireless communication sniffing.

5. The method of claim 1 wherein passively detecting wake-up signals is performed using wireless signal reception components of the implantable medical device and wherein, in the absence of detection of a wake-up signal warranting a response, the wireless signal reception components of the implantable medical device enter a sleep mode pending a next passive detection cycle.

6. The method of claim 1
    wherein passively detecting short range wireless communication wake-up signals generated by an external instrument includes initiating a passive scan search period and, during at least a portion of the scan search period, sniffing for any wireless wake-up signals generated by instruments that are external to the patient; and
    wherein, if at least one wireless wake-up signal is detected during the scan search period, then waiting until completion of the scan search period before activating the short range wireless signal transmission components and transmitting the acknowledgement signal to the external instrument that generated the detected wireless wake-up signal.

7. The method of claim 1 wherein determining if a response to the wake-up signal is warranted includes determining if a particular software component of the particular external instrument generating the wake-up signal is authorized to wake up the implantable medical device based on a coded signal received from the external instrument that indicates the particular software component is authorized to wake up the implantable medical device and that differs from coded signals associated with at least some other software components capable of generating coded signals for transmission to the implantable medical device but not authorized to wake up the implantable medical device.

8. The method of claim 1 wherein the wake-up signal includes identifying information for identifying the external instrument or a component thereof and additional information beyond the identifying information and wherein, if a response to the wake-up signal is warranted, the implantable medical device also responds to the additional information.

9. A method for use by an implantable medical device for implant within a patient and an external instrument equipped to communicate with the implantable medical device, the method comprising:
    generating wireless wake-up signals using the external instrument;
    passively detecting the wireless wake-up signals generated by the external instrument using the implantable medical device where the external instrument is one of a plurality of external instruments capable of communicating with the implantable medical device, and wherein at least some of the plurality of external instruments are not authorized to communicate with the implantable medical device;
    in response to passive detection of a wake-up signal by the implantable medical device, determining if a response to the wake-up signal is warranted and, if so, activating wireless signal transmission components of the implantable medical device and transmitting an acknowledgement signal to the external instrument, wherein determining if a response to the wake-up signal is warranted includes determining if the external instrument is authorized to wake up the implantable medical device based on a coded signal received from the external instrument that indicates the external instrument is authorized to wake up the implantable medical device and that differs from coded signals from at least some other external instruments capable of communicating with the implantable medical device but not authorized to wake up the implantable medical device; and
    in response to detection by the external instrument of the acknowledgement signal, engaging in further wireless communications between the external instrument and the implantable medical device.

10. The method of claim 9 wherein the wake-up signals are short range wireless wake-up signals received by a component of the implantable medical device.

11. The method of claim 10 wherein the short range wireless wake-up signals generated by the external instrument are advertisement signals generated in accordance with a low energy short range wireless communication standard.

12. The method of claim 10 wherein the passive detection of wake-up signals by the implantable medical device includes short range wireless sniffing.

13. The method of claim 9 wherein passive detection of wake-up signals by the implantable medical device is performed using wireless signal reception components of the implantable medical device and wherein, in the absence of detection of a wake-up signal warranting a response, the wireless signal reception components of the implantable medical device enter a sleep mode pending a next passive detection cycle.

14. A system for use by an implantable medical device for implant within a patient, the system comprising:
  passive signal reception components operative to passively detect wireless wake-up signals generated by an external instrument equipped to communicate with the implantable medical device where the external instrument is one of a plurality of external instruments capable of communicating with the implantable medical device, wherein at least some of the plurality of external instruments are not authorized to communicate with the implantable medical device;
  wake-up signal processing components operative in response to passive detection of a wake-up signal from the external instrument to determine if a response is warranted including determining if the external instrument generating the wake-up signal is authorized to wake up the implantable medical device based on a coded signal received from the external instrument that indicates the external instrument is authorized to wake up the implantable medical device and that differs from coded signals from at least some other external instruments capable of communicating with the implantable medical device but not authorized to wake up the implantable medical device; and
  active signal transmission components operative if a response is warranted to transmit a wireless acknowledgement signal to the external instrument.

15. The system of claim 14
  wherein the passive signal reception components are further operative to initiate a passive scan search period and, during at least a portion of the scan search period, sniff for any wireless wake-up signals generated by instruments that are external to the patient; and
  wherein the active signal transmission components are further operative, in response to detection of at least one wireless wake-up signal during the scan search period, to wait until completion of the scan search period before transmitting the acknowledgement signal to the external instrument that generated the detected wireless wake-up signal.

16. The system of claim 14 wherein the wake-up signal processing components are further operative to determine if a particular software component of the particular external instrument generating the wake-up signal is authorized to wake up the implantable medical device based on a coded signal received from the external instrument that indicates the particular software component is authorized to wake up the implantable medical device and that differs from coded signals associated with at least some other software components capable of generating signals for transmission to the implantable medical device but not authorized to wake up the implantable medical device.

17. The system of claim 14 wherein the wake-up signal includes identifying information for identifying the external instrument or a component thereof and additional information beyond the identifying information and wherein the system is further operative to respond to the additional information.

18. The system of claim 14, wherein the wake-up signals are short range wireless wake-up signals received by a component of the implantable medical device.

19. A method for use by a trial medical device having at least one lead for implant within a patient, the method comprising:
  passively detecting wireless wake-up signals generated by an external instrument equipped to communicate with the trial medical device where the external instrument is one of a plurality of external instruments capable of communicating with the trial medical device, wherein at least some of the plurality of external instruments are not authorized to communicate with the trial medical device; and
  in response to passive detection of a wake-up signal from the external instrument, determining if a response is warranted and, if so, activating wireless signal transmission components of the trial medical device and transmitting an acknowledgement signal to the external instrument, wherein determining if a response to the wake-up signal is warranted includes determining if the external instrument generating the wake-up signal is authorized to wake up the trial medical device based on a coded signal received from the external instrument that indicates the external instrument is authorized to wake up the trial medical device and that differs from coded signals from at least some other external instruments capable of communicating with the trial medical device but not authorized to wake up the trial medical device.

20. The method of claim 19
  wherein passively detecting short range wireless communication wake-up signals generated by an external instrument includes initiating a passive scan search period and, during at least a portion of the scan search period, sniffing for any wireless wake-up signals generated by instruments that are external to the patient; and
  wherein, if at least one wireless wake-up signal is detected during the scan search period, then waiting until completion of the scan search period before activating the short range wireless signal transmission components and transmitting the acknowledgement signal to the external instrument that generated the detected wireless wake-up signal.

21. The method of claim 19 wherein determining if a response to the wake-up signal is warranted includes determining if a particular software component of the particular external instrument generating the wake-up signal is authorized to wake up the trial medical device based on a coded signal received from the external instrument that indicates the particular software component is authorized to wake up the trial medical device and that differs from coded signals associated with at least some other software components capable of generating signals for transmission to the implantable medical device but not authorized to wake up the trial medical device.

22. The method of claim 19 wherein the wake-up signal includes identifying information for identifying the external instrument or a component thereof and additional information beyond the identifying information and wherein, if a response to the wake-up signal is warranted, the trial medical device also responds to the additional information.

23. A method for use by a trial medical device having at least one lead for implant within a patient and an external instrument equipped to communicate with the trial medical device, the method comprising:
  generating wireless wake-up signals using the external instrument;
  passively detecting the wireless wake-up signals generated by the external instrument using the trial medical device where the external instrument is one of a plurality of external instruments capable of communicating with the trial medical device, and wherein at least some of the plurality of external instruments are not authorized to communicate with the trial medical device;
  in response to passive detection of a wake-up signal by the trial medical device, determining if a response is warranted and, if so, activating wireless signal transmission components of the trial medical device and transmitting an acknowledgement signal to the external instrument, wherein determining if a response to the wake-up signal is warranted includes determining if the external instrument generating the wake-up signal is authorized to wake up the trial medical device based on a coded signal received from the external instrument that indicates the external instrument is authorized to wake up the trial medical device and that differs from coded signals from at least some other external instruments capable of communicating with the trial medical device but not authorized to wake up the trial medical device; and
  in response to detection by the external instrument of the acknowledgement signal, engaging in further wireless communications between the external instrument and the trial medical device.

* * * * *